(12) United States Patent
Sparks et al.

(10) Patent No.: US 8,593,155 B2
(45) Date of Patent: Nov. 26, 2013

(54) MEMS IN-PLANE RESONATORS

(75) Inventors: Andrew Sparks, Cambridge, MA (US); Milind Bhagavat, Medford, MA (US)

(73) Assignee: Analog Devices, Inc., Norwood, MA (US)

( * ) Notice: Subject to any disclaimer, the term of this patent is extended or adjusted under 35 U.S.C. 154(b) by 571 days.

(21) Appl. No.: 12/853,619

(22) Filed: Aug. 10, 2010

(65) Prior Publication Data

US 2012/0112765 A1 May 10, 2012

Related U.S. Application Data

(60) Provisional application No. 61/233,581, filed on Aug. 13, 2009.

(51) Int. Cl.
*G01R 27/04* (2006.01)

(52) U.S. Cl.
USPC ........................................................... 324/633

(58) Field of Classification Search
USPC .......................................... 324/633, 629, 600
See application file for complete search history.

(56) References Cited

U.S. PATENT DOCUMENTS

| | | | | |
|---|---|---|---|---|
| 4,809,589 | A | 3/1989 | Bertrand | 92/98 R |
| 5,177,579 | A | 1/1993 | Jerman | 73/724 |
| 5,589,082 | A | 12/1996 | Lin et al. | 216/2 |
| 5,750,899 | A | 5/1998 | Hegner et al. | 73/756 |
| 5,937,275 | A | 8/1999 | Munzel et al. | 438/50 |
| 5,992,233 | A | 11/1999 | Clark | 73/514.35 |
| 6,635,509 | B1 | 10/2003 | Ouellet | 438/106 |
| 6,892,575 | B2 * | 5/2005 | Nasiri et al. | 73/504.12 |
| 6,985,051 | B2 | 1/2006 | Nguyen et al. | 333/186 |
| 7,032,451 | B2 | 4/2006 | Geen | 73/504.14 |
| 7,051,590 | B1 | 5/2006 | Lemkin et al. | 73/504.04 |
| 7,178,378 | B2 | 2/2007 | Crawley et al. | 73/24.06 |
| 7,427,819 | B2 | 9/2008 | Hoen et al. | 310/320 |
| 7,492,241 | B2 | 2/2009 | Piazza et al. | 333/189 |
| 7,551,043 | B2 | 6/2009 | Nguyen et al. | 333/186 |

(Continued)

FOREIGN PATENT DOCUMENTS

| | | | |
|---|---|---|---|
| EP | 1788385 | 5/2007 | G01N 29/02 |
| EP | 2216904 | 9/2010 | H03H 9/25 |
| WO | 2009066640 | 5/2009 | H03H 9/25 |

OTHER PUBLICATIONS

Bill Drafts "Acoustic Wave Technology Sensors," Sensors (www.sensorsmag.com), 8 pages, Oct. 1, 2000.

(Continued)

*Primary Examiner* — Hoai-An D Nguyen
(74) *Attorney, Agent, or Firm* — Sunstein Kann Murphy & Timbers LLP

(57) ABSTRACT

MEMS in-plane resonators include a substrate wafer, at least one resonant mass supported by the substrate wafer and configured to resonate substantially in-plane, and at least one transducer coupled to the at least one resonant mass for at least one of driving and sensing in-plane movement of the at least one resonant mass, wherein at least part of one surface of the resonant mass is configured for exposure to an external environment and wherein the at least one transducer is isolated from the external environment. Such MEMS in-plane resonators may be fabricated using conventional surface micromachining techniques and high-volume wafer fabrication processes and may be configured for liquid applications (e.g., viscometry, densitometry, chemical/biological sensing), gas sensing (e.g., where a polymer film is added to the sensor surface, further degrading the damping performance), or other applications.

24 Claims, 13 Drawing Sheets

(56) References Cited

U.S. PATENT DOCUMENTS

| | | | |
|---|---|---|---|
| 2003/0119220 A1 | 6/2003 | Mlcak et al. | 438/52 |
| 2003/0183888 A1 | 10/2003 | Bar-Sadeh et al. | 257/419 |
| 2004/0051595 A1 | 3/2004 | Yoshimine et al. | 331/158 |
| 2005/0148065 A1 | 7/2005 | Zhang et al. | 435/287.2 |
| 2006/0133953 A1 | 6/2006 | Zhang et al. | 422/58 |
| 2006/0196253 A1 | 9/2006 | Crawley et al. | 73/53.01 |
| 2006/0237806 A1 | 10/2006 | Martin et al. | 257/415 |
| 2007/0046398 A1 | 3/2007 | Nguyen et al. | 333/186 |
| 2007/0172940 A9 | 7/2007 | Manalis et al. | 435/287.2 |
| 2008/0190181 A1 | 8/2008 | Khuri-Yakub et al. | 73/64.53 |
| 2008/0282833 A1 | 11/2008 | Chaumet | 74/5 R |
| 2009/0114016 A1* | 5/2009 | Nasiri et al. | 73/504.12 |
| 2009/0173158 A1 | 7/2009 | Gehring | 73/590 |
| 2009/0277271 A1 | 11/2009 | Seppa et al. | 73/627 |
| 2010/0263445 A1* | 10/2010 | Hayner et al. | 73/504.12 |
| 2011/0192226 A1* | 8/2011 | Hayner et al. | 73/504.12 |

OTHER PUBLICATIONS

Marc-Alexandre Dubois "Thin film bulk acoustic wave resonators: a technology overview," MEMSWAVE 03, Toulouse, France, 4 pages, Jul. 2-4, 2003.

Saukoski "System and Circuit Design for a Capacitive MEMS Gyroscope," Doctoral Dissertation, TKK Dissertations 116, Helsinki University of Technology, 279 pages (2008).

International Searching Authority, International Search Report—International Application No. PCT/US2010/044994, dated Nov. 3, 2010, together with the Written Opinion of the International Searching Authority, 11 pages.

* cited by examiner

LTO (spacer oxide) and Densification & Patterning

Polysilicon deposition and planarization

Pattern the oxide

Polysilicon cap layer deposition

Pattern polysilicon for release etch holes and to define the springs

Release Etch (Vapor HF)

Some oxide may remain between shield and sense, and shield & drive electrodes

MEMS IN-PLANE RESONATORS

CROSS-REFERENCE TO RELATED APPLICATION(S)

This application claims the benefit of U.S. Provisional Patent Application No. 61/233,581 entitled MEMS IN-PLANE RESONATORS filed on Aug. 13, 2009, which is hereby incorporated herein by reference in its entirety.

FIELD OF THE INVENTION

The present invention relates generally to MEMS devices and, in particular, to MEMS in-plane resonators.

BACKGROUND OF THE INVENTION

Sensors based of mechanically resonant elements have long been of interest due to their high sensitivity and electrical readout capability. Resonant sensors allow the use of resonant frequency and/or quality factor (Q) to detect such things as mass, stiffness, and/or damping changes at the resonator surfaces. Applications for such sensors are broad and include, among other things, inertial, pressure, temperature, strain, flow rate, viscosity, density, and chemical/biological sensors.

Many of these sensors are currently constructed from quartz or other piezoelectric materials. Although their performance is proven, they are difficult to miniaturize, integrate, and optimize in a high-volume wafer fabrication process, such as that commonly used to make silicon-based integrated circuits.

A major limitation of resonant sensors exposed to a nonvacuum environment is the performance degradation from viscous damping through various physical mechanisms. The damping directly lowers the Q and therefore the detection limits of the device.

One way that the piezoelectric community has addressed this performance degradation is by constructing crystals with shear (in-plane) vibration modes. Analogous to rowing a boat with the edge of an oar instead of the face, much less force is exerted by the fluid on the mechanical element (and vice versa), and therefore the damping can be minimized. Piezoelectric materials include metal electrodes on two sides for transduction, so placing them in liquids or harsh gaseous environments can require sophisticated passivation or packaging strategies, which can affect both performance and cost. Capacitive transduction, which is favored among non-piezoelectric micromechanical resonators for its simplicity and sensitivity, would also be adversely affected by the presence of fluid or changing environmental conditions. Other transduction methods have their own drawbacks related to cost, performance, interfacing with the sense environment, and/or integration.

There is considerable effort in the MEMS industry to manufacture MEMS resonators (typically silicon) to create frequency references and filters that would compete with conventional quartz devices. However, these devices generally require that all resonator surfaces be packaged in a vacuum with no external environmental exposure. Sealing of these devices can be achieved by capping at low pressures.

Some exemplary efforts to commercialize biosensors based on microscale resonators include piezoelectric devices (e.g., BioScale, Inc. Ser. No. 07/178,378, US2006/0196253, Boston Microsystems US2003/0119220, and Intel US2006/0133953) that require exotic materials (compared to silicon) and passivation schemes, and microchannel resonators (e.g., MIT/Affinity Biosensors, US2007/0172940) that require all fluids of interest to flow through a micron-scale resonant channel as well as functionalization of internal surfaces.

The pressure sensor community demonstrated corrugated diaphragms with isolated capacitive transduction as early as the 1980s (e.g., U.S. Pat. No. 5,750,899, US2003/0183888, U.S. Pat. No. 4,809,589, U.S. Pat. No. 5,177,579), but these devices move out-of-plane and therefore generally would suffer from overwhelming damping in fluid environments.

Likewise, capacitive micromachined ultrasonic transducers (CMUTs), which resonate out-of-plane, have been used for gas sensing and proposed for liquid sensing (e.g., Stanford University, US2008/0190181) but generally have similar damping limitations.

"In-situ capping" is currently being pursued by several companies to hermetically seal MEMS devices at the wafer scale (e.g., SiTime, in collaboration with Bosch, in an effort to build all-vacuum-encapsulated resonators). Some of the in-situ capping patents in public domain include U.S. Pat. No. 6,635,509 filed by Dalsa Semiconductors, U.S. Pat. No. 5,589,082 filed by University of California Regents, and U.S. Pat. No. 5,937,275 filed by Bosch. Also a European Government sponsored project SUMICAP had some work done on this aspect. However, in the above literature, the main purpose has been to provide a rigid cap to the devices to act as protection.

Resonators have been used for biological/chemical sensing, viscometry, and similar applications. For example, the quartz crystal microbalance (QCM) was demonstrated as a mass sensor in 1959. Since then, it has become a common analytical tool in the chemical and biological sciences for use in vacuum, gas, and liquid environments. Typically, such sensors are relatively large (e.g., centimeters across by hundreds of microns thick), and this relatively large size tends to limit their mass resolution. However, QCM is a pervasive laboratory tool for biosensing, chemical sensing, viscometry, etc.

Silicon-based lateral resonators for liquid applications have been demonstrated utilizing piezoresistive detection without isolating part of the device from the liquid such that the devices may be susceptible to particles that can be trapped under the resonant mass.

A lateral resonator with exposed electrodes is described in U.S. Pat. No. 7,551,043 filed by Nguyen et al.

Each of the above-referenced patents and published patent applications is hereby incorporated herein by reference in its entirety.

SUMMARY OF THE INVENTION

Embodiments of the present invention include MEMS in-plane resonators that can be fabricated using conventional surface micromachining techniques and high-volume wafer fabrication processes. Such MEMS in-plane resonators may be particularly useful for liquid applications (e.g., viscometry, densitometry, chemical/biological sensing) and gas sensing (e.g., where a polymer film is added to the sensor surface, further degrading the damping performance).

Various embodiments may include some or all of the following:

a. The concept of a MEMS in-plane resonator with at least part of one surface (henceforth referred to as the "ambient interface") exposed to the surrounding environment (whether gas, liquid, or vacuum), and the other surfaces ("hermetic interface") hermetically isolated from the surrounding environment. Various resonant modes are disclosed, including flexural, bulk acoustic, and rotational.

b. The ability to use capacitive transduction in liquid or harsh environments without degrading the transduction or affecting the environment. Conductive surfaces in contact with the ambient can have a predetermined electrical potential applied (e.g., a zero potential that may reduce or eliminate electrochemical interactions in some circumstances or a non-zero potential to encourage electrochemical interactions).

c. The placement of capacitive transducers in such a way that they excite in-plane vibration modes, as preferred in a viscous environment. Acoustic modes of interest include, but are not limited to, bulk "contour" and flexural modes. Depending on the design and process, anchoring may occur at one or more points on the proof mass and to a structure within the plane of the mass or normal to this plane. The choice of mode shape is essentially restricted only by the goal of achieving predominately in-plane motion.

d. The placement of capacitive transducers in such a way that they are electrically shielded from both the ambient interface and all necessary circuit elements, allowing the use of high voltages, if necessary to improve the performance, and eliminating electrokinetic effects in the sense environment.

e. The ability to maintain a low gas pressure at the hermetic interface, resulting in less overall damping and lower detection limits, while not affecting the ambient interface.

f. The use of a sealing process to achieve hermetic isolation of the transducers.

g. The use of springs to provide lateral compliance and/or relieve stress generated by the sealing process. These springs can be either compliant flexures (e.g. corrugations) made of the same material as the resonator (e.g. silicon), or they can be "plugs" of a second material with a lower Young's modulus than the resonator material. The springs can be designed to help suppress out-of-plane motion.

h. Overall robustness of the design—the resonator is relatively stiff and resistant to particulates and residue from the environment (due to minimal exposed surface area).

i. Minimal topography at the ambient interface, reducing the likelihood of bubble and particle trapping.

j. Advantages from miniaturization including sensitivity, cost, and the feasibility of arrays of well-matched sensors.

These and other aspects are discussed in the detailed description below.

In accordance with one aspect of the invention there is provided a MEMS sensor comprising a substrate wafer, at least one resonant mass supported by the substrate wafer and configured to resonate substantially in-plane, and at least one transducer coupled to the at least one resonant mass for at least part of one of driving and sensing in-plane movement of the at least one resonant mass, wherein at least part of one surface of the resonant mass is configured for exposure to an external environment and wherein the at least one transducer is isolated from the external environment.

As discussed herein, such a MEMS sensor may be configured for operation as a viscometer, densitometer, chemical sensor, biological sensor, gas sensor, or any of various other types of sensors. Transducers may include capacitively-coupled transducers, piezoelectrically-coupled transducers, and/or other types of transducers.

In various alternative embodiments, the at least one transducer may be at least partially contained within an isolated cavity formed in part or in whole by the at least one resonant mass and the substrate wafer. For example, the at least one resonant mass may be part of a resonator cap attached to the substrate wafer, and the resonator cap and the substrate wafer may form an isolated cavity within which the at least one transducer is at least partially contained. Such as resonator cap may be formed in situ with the wafer (e.g., using various MEMS deposition, patterning, and etching processes) or may be formed separately and then bonded directly or indirectly to the wafer, e.g., using various wafer-to-wafer bonding techniques. Certain embodiments may include a hermetic seal at an interface between the resonator cap and the substrate wafer (e.g., the bonding material may be hermetic, or a non-hermetic bonding material may be sealed with a hermetic material). The cavity may be partially or completely evacuated if desired to lower the overall damping.

In other alternative embodiments, the resonant mass may be movably coupled to the at least one transducer via an elastic material, and portions of the at least one transducer that would otherwise be exposed to the external environment may be covered with at least one material to isolate those portions from the external environment.

Additionally or alternatively, a top side of the resonant mass may be configured for exposure to the external environment and a bottom side of the resonant mass may include at least one protrusion configured to interoperate with the at least one transducer for at least one of driving and sensing in-plane movement of the resonant mass. The transducer may be capacitively coupled with the protrusion or may interoperate with the protrusion using other techniques, e.g., the transducer may be a piezoelectric transducer that is mechanically coupled with the protrusion. The resonant mass may be configured to resonate translationally in-plane, rotationally in-plane, in a bulk acoustic contour mode in-plane (e.g., with anchoring at one or more locations on the mass to structures in the plane of the mass or normal to the plane of the mass), or otherwise. The resonant mass may be round (e.g., a disk or annular), square, or other shape.

Additionally or alternatively, a set of shield structures may be included on the substrate wafer.

Additionally or alternatively, the sensor may include circuitry configured to apply a predetermined electrical potential to at least one outer conductive surface exposed to the external environment. For example, the circuitry may apply a zero potential, a non-zero potential, or a variable potential to the top surface of the resonant mass or to the entire resonator cap.

Additionally or alternatively, the at least one resonant mass may be movably coupled by a suspension. For example, the suspension may include a spring (e.g., a notched spring, a serpentine spring, or an in-line spring) or an elastic plug (e.g., having a lower Young's modulus than the resonant mass material). Top side notches in a spring may be filled with an elastic material.

Additionally or alternatively, the surface of at least one resonant mass configured for exposure to the external environment may be at least partially covered by a material meant to interact with a specific type of target (e.g., ligand) in the external environment, where such interaction changes the moving mass of the resonant mass so as to change the resonance frequency of the resonant mass, and the sensor may include circuitry configured to detect such a change in resonance frequency resulting from such interaction. The interaction may increase or decrease the moving mass and therefore may decrease or increase the resonance frequency of the resonant mass. The circuitry may be configured to determine the presence of the target, the amount of the target, and/or other attributes such as a specific type of target. The material may include such things as an adhesive material to which the target adheres, a chemically or electrochemically active material, a hydrophilic material, a receptor material to which a specific target binds, and/or a material that dissolves or dissipates in the presence of the target (e.g., moisture, acid, etc) so as to decrease the moving mass of the resonator and consequently increase the resonance frequency of the resonator, to name but a few.

Additionally or alternatively, the surface of at least one resonant mass configured for exposure to the external environment may be at least partially covered by a material meant to reduce interactions with the external environment. The material may include such things as a passivation material (e.g., to prevent damage from exposure to certain chemicals, radiation, etc.), an anti-stiction material, a hydrophobic material, an electrical conductor or insulator material, and/or a polymer film that further degrades the damping performance (e.g., for gas sensing applications), to name but a few.

Additionally or alternatively, the sensor may include circuitry configured to sense an electrical potential caused by interaction with the external environment. For example, an electrical charge may be produced when the sensor is in the presence of certain chemicals, and this electrical charge can be detected and characterized to determine such things as the presence, amount, and/or type of chemical.

Additionally or alternatively, the at least one resonant mass may include raised and/or recessed features patterned or otherwise formed on of from the top surface of the resonant mass. For example, the features may include corrugations, bumps, dimples, or other features. Such features may increase the surface area exposed to the external environment (e.g., to improve chemical/biological interactivity), increase or reduce friction with the external environment (e.g., to agitate a fluid), and/or stiffen the resonant mass. Sensors may be formed with microfluidic networks and/or active sensors, e.g., to support lab-on-a-chip and other applications. A microfluidic network may include such things as channels, pumps, valves, and other elements. Sensors may include electronic, mechanical, chemical, biological, drug, and other types of sensors.

Additionally or alternatively, the sensor may include at least one transducer coupled to the at least one resonant mass for at least one of driving and sensing out-of-plane movements of the at least one resonant mass. For example, the transducer may be used to sense out-of-plane movements of the resonant mass (e.g., to incorporate a pressure sensor with other sensor functions such as target detection) and/or may be used to drive out-of-plane movements of the resonant mass (e.g., to compensate for erroneous out-of-plane motion).

In certain embodiments, a MEMS sensor may include a plurality of resonant masses which may operate independently or cooperatively. For example, the resonant masses may be mechanically and/or electrically coupled. Resonant masses may include the same functional coatings (e.g., for redundancy in detecting a target and environmental characteristic) or different functional coatings (e.g., for detecting different targets or environmental characteristics).

In accordance with another aspect of the invention, a plurality of MEMS sensors of the types described herein may be formed on a single wafer. Thus, embodiments of the present invention include apparatus comprising an array of a plurality of MEMS sensors.

In various alternative embodiments, at least two sensors may be of the same mechanical design, at least two sensors may be of different mechanical designs, at least two sensors may have the same functional coating, at least two sensors may have different functional coatings, at least two sensors may be mechanically coupled, and/or at least two sensors may be electrically coupled.

In accordance with yet another aspect of the invention there is provided a method of fabricating a MEMS in-plane resonator comprising forming at least one resonant mass supported by a substrate wafer and configured to resonate substantially in-plane; and forming at least one transducer coupled to the at least one resonant mass for at least one of driving and sensing in-plane movement of the at least one resonant mass, wherein at least one surface the resonant mass is configured for exposure to an external environment and wherein the at least one transducer is isolated from the external environment.

The method may include some or all of the fabrication steps described with reference to FIG. 2 and optionally additional or alternative fabrication steps. The method may be adapted for producing sensors with different types of resonator masses, transducers, material coatings, circuitry, and other elements.

BRIEF DESCRIPTION OF THE DRAWINGS

The foregoing and advantages of the invention will be appreciated more fully from the following further description thereof with reference to the accompanying drawings wherein.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Figure 1:
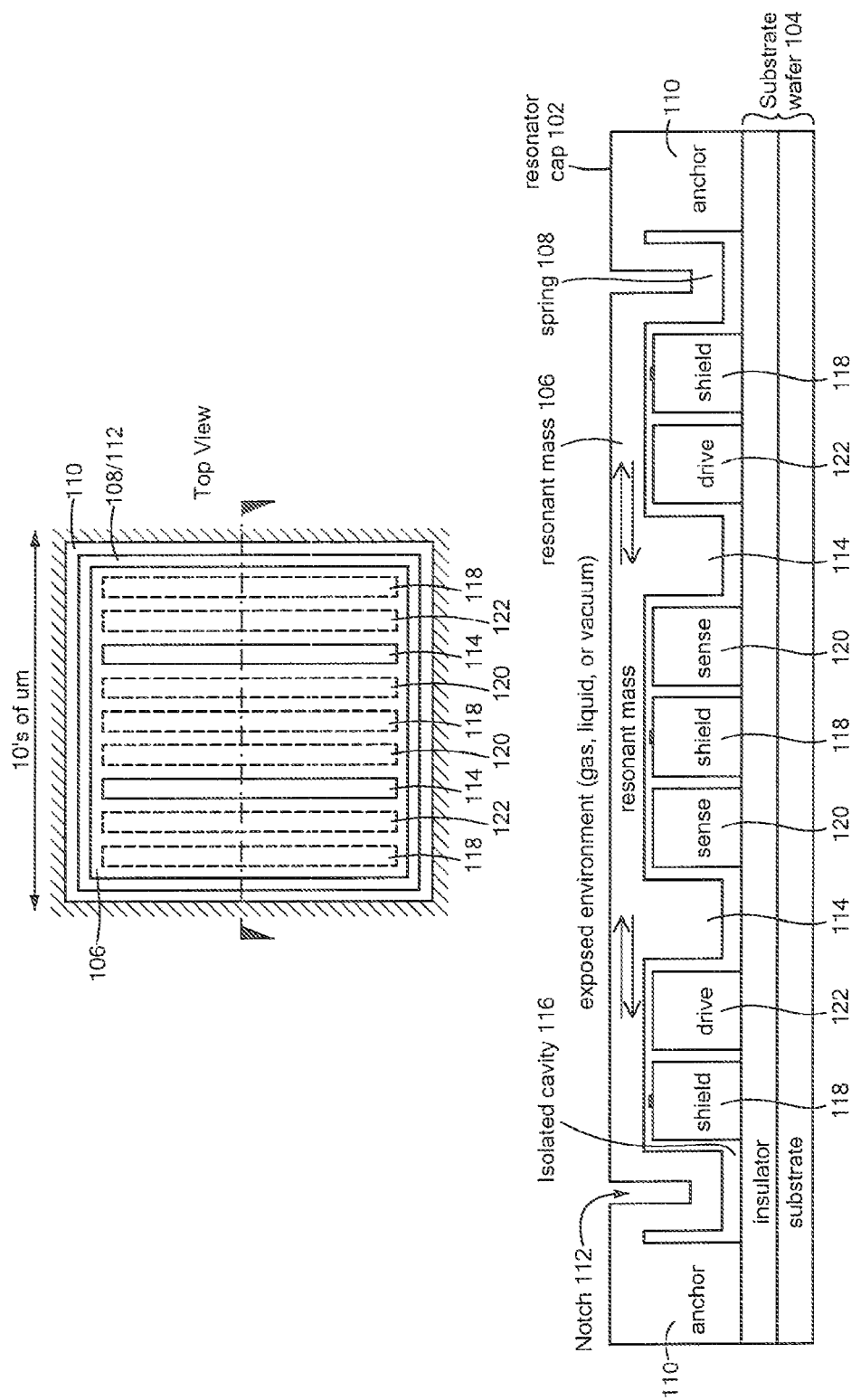
FIG. 1 is a schematic diagram showing top and cross-sectional views of a MEMS in-plane resonator that operates in a flexural mode, in accordance with an exemplary embodiment of the present invention.

Definitions. As used in this description and the accompanying claims, the following terms shall have the meanings indicated, unless the context otherwise requires:

A "set" includes one or more members.

The term "in-plane" should be understood to mean predominately in the plane of the resonator wafer and/or sensing surface. Typically, a small amount of out-of-plane motion will be present, for example, due to the Poisson effect, fabrication variations, etc., and generally can be tolerated.

The "mode" of a resonating body is the shape of motion of the body at resonance.

An "electrode" is a structure through which an electrical or electromechanical effect is applied and/or sensed. In exemplary embodiments, various electrodes are used for applying and/or sensing electrical or electromechanical effects through capacitive coupling (e.g., between a resonant mass and one or more adjacent structures), although it should be noted that other types of electrodes and couplings may be used (e.g., piezoelectric). Thus, in exemplary embodiments, electrodes may include a resonant mass and one or more structures for driving and/or sensing movement of the resonant mass.

A structure may be "attached" to another structure by being directly or indirectly formed on or bonded to the other structure. Thus, for example, a cap may be attached to a wafer by being formed directly or indirectly on the wafer in situ (e.g., using MEMS processes of depositing, patterning, and etching materials) or a cap may be attached to a wafer by being bonded directly or indirectly to the wafer.

In exemplary embodiments of the present invention, a MEMS in-plane resonator includes a cap with an integral resonant mass that is configured to resonate substantially within a device plane (e.g., laterally, rotationally, in a bulk acoustic mode, or otherwise) above an underlying substrate wafer. Purely for the sake of convenience, the cap with integral resonant mass may be referred to hereinafter as a "resonator cap." The resonator cap may be formed along with the other structures on the substrate wafer in situ or may be bonded to the substrate wafer using any of a variety of wafer-to-wafer bonding techniques. Among other things, the in-plane movement of the resonant mass tends to minimize viscous damping associated with the external environment and may be useful in other contexts in which out-of-plane resonance would be undesirable.

Typically, at least part of one surface of the resonant mass (which may be referred to hereinafter as the "ambient interface") is exposed to the surrounding environment (e.g., gas, liquid, or vacuum), and the other surfaces (which may be referred to hereinafter as the "hermetic interface") are hermetically isolated from the surrounding environment within, or as part of, a hermetically sealed cavity.

The hermetically-sealed cavity houses various components such as, for example, electrical and mechanical components used to drive and sense the motion of the resonant mass in the device plane (e.g., capacitive/electrostatic transducers and/or piezoelectric transducers). Thus, such embodiments of the present invention generally enable such transducers to be used in liquid or harsh environments without degrading the transduction. It should be noted that, in addition to housing the drive and/or sense transducers for the resonant mass, the sealed cavity also tends to reduce the overall damping of the device (particular in embodiments in which the cavity is evacuated) and also prevents contaminants (including bubbles) from getting underneath the resonator and affecting its performance.

Various embodiments of the present invention may be fabricated using conventional surface micromachining techniques and high-volume wafer fabrication processes, widespread for fabricating MEMS sensors, to construct in-plane resonators exposed to an external environment with hermetically isolated transducers. Such a high-volume process also enables arrays of sensors to be fabricated on the same centimeter- or millimeter-scale chip with optionally integrated electronics, providing generally better selectivity and robustness as well as enhanced algorithms for signal conditioning. Thus, embodiments of the present invention may include MEMS in-plane resonators smaller than a few centimeters across and less than a few millimeters thick, allowing such device to be fabricated in large volumes and enabling their use in applications where small size is necessary or desirable.

FIG. 1 is a schematic diagram showing top and cross-sectional views of a MEMS in-plane resonator 100 that operates in a flexural mode, in accordance with an exemplary embodiment of the present invention. The MEMS in-plane resonator 100 includes a resonator cap 102 attached to an underlying substrate wafer 104 that includes elongated drive electrodes 122, sense electrodes 120, and shield structures 118 formed above an insulator layer. The resonator cap 102 includes resonant mass 106 movably coupled to anchors 110 by springs 108 having top-side notches 112 (for convenience, only one spring and one notch is numbered). The underside of the resonant mass 106 includes elongated protrusions 114 that are capacitively coupled with the drive electrodes 122 and sense electrodes 120 to respectively drive and sense lateral resonance of the resonant mass 106. The shield structures 118 provide electrical shielding in appropriate places, such as between the two middle sense electrodes 120 and between the drive electrodes 122 and the notched springs 108. In the top view, the vertically-oriented rectangles shown in dashed lines represent the drive, sense, and shield structures while the vertically-oriented rectangles shown in solid lines represent the protrusions 114. As shown in the top view, the resonant mass 106 is substantially square and is surrounded on all four sides by notched springs and surrounding anchors so as to form an isolated cavity 116 that houses the drive 122, sense 120, and shield 118 structures. For convenience, various structures are omitted from FIG. 1 such as, for example, electrical connections to the drive electrodes 122, sense electrodes 120, shield structures 118, and resonator cap 102.

FIG. 2 is a conceptual process flow of a MEMS fabrication process for producing a MEMS in-plane resonator of the type shown in FIG. 1, in accordance with an exemplary embodiment of the present invention.

Figure 2A:
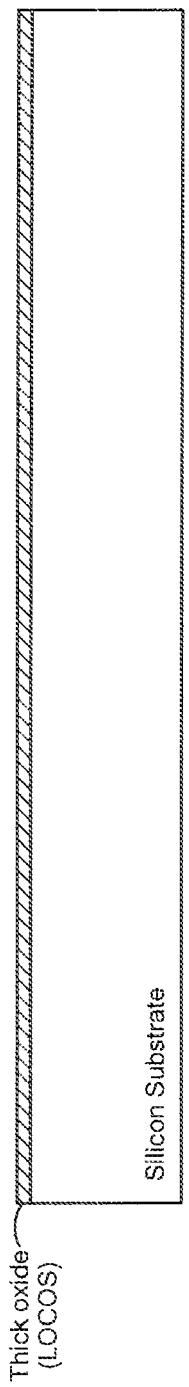
FIG. 2 is a conceptual process flow of a MEMS fabrication process for producing a MEMS in-plane resonator of the type shown in FIG. 1, in accordance with an exemplary embodiment of the present invention.

In FIG. 2A, an oxide layer is formed on the substrate. In this example, the substrate is a silicon substrate and the oxide layer is formed using a LOCOS (local oxidation of silicon) process. Alternatively, an oxide material may be deposited or otherwise formed on the substrate.

Figure 2B:
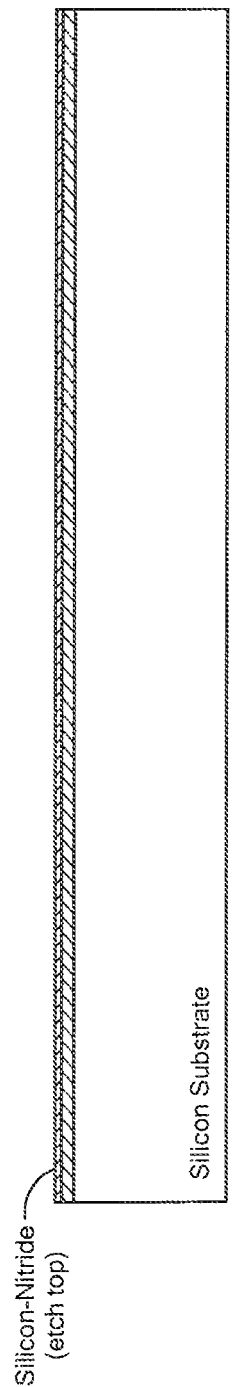

In FIG. 2B, a silicon nitride etch stop layer is formed on the oxide layer.

Figure 2C:
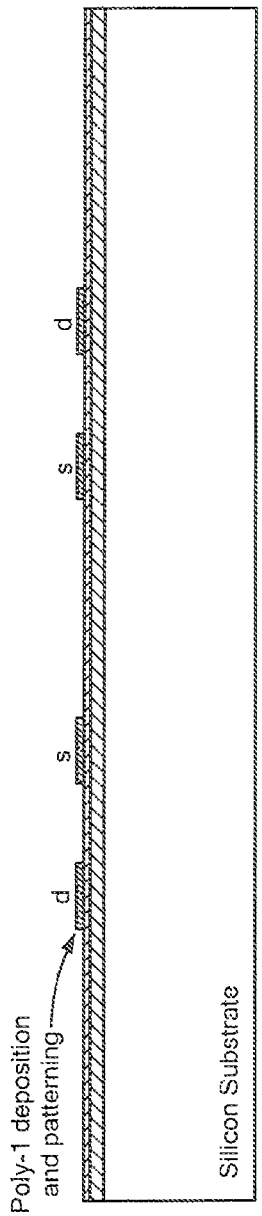

In FIG. 2C, a polysilicon layer is deposited and patterned to form the elongated drive and sense electrodes.

Figure 2D:
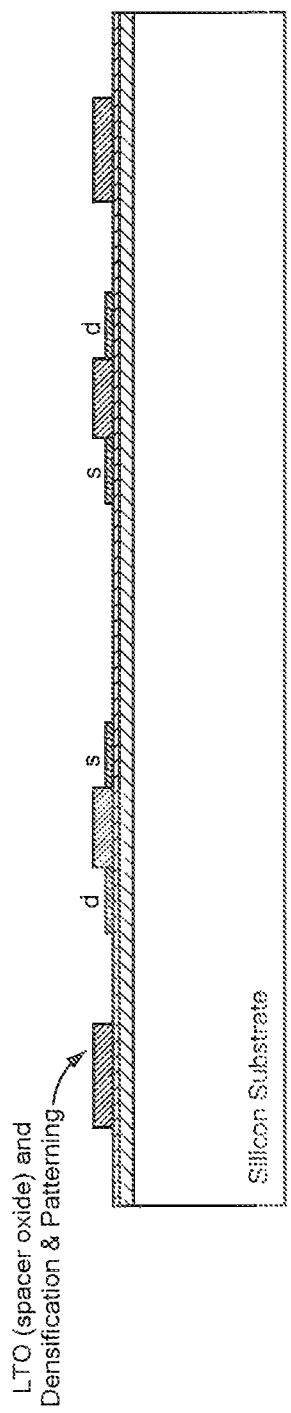

In FIG. 2D, oxide spacers are formed essentially where the springs 108 and protrusions 114 will be located, in this case, by depositing oxide using a LTO (low temperature oxide) deposition process, performing a densification process, and then patterning the oxide to form the spacers.

Figure 2E:
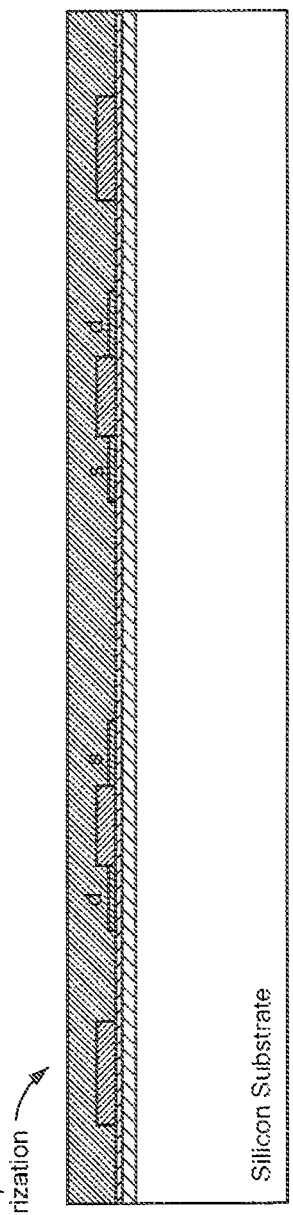

In FIG. 2E, a polysilicon layer is deposited and planarized. This polysilicon layer will form portions of the anchors 110 and shields that are attached to the substrate wafer as well as portions of the protrusions 114 on the underside of the resonant mass 106.

Figure 2F:
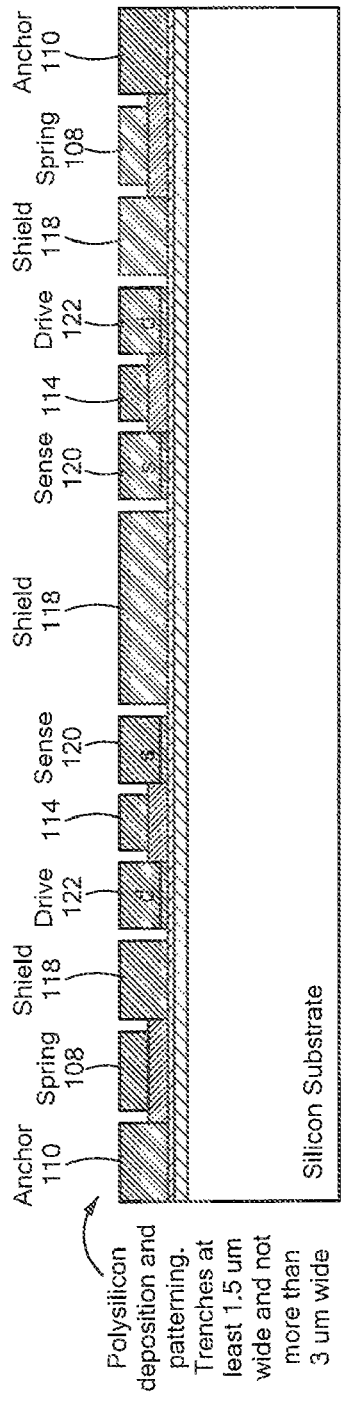

In FIG. 2F, trenches are formed in the polysilicon layer essentially where spaces will exist between the various structures, such as between the anchor and springs, between the springs and the shields, between the shields and the drive/sense electrodes, and between the drive/sense electrodes and the protrusions 114. In an exemplary embodiment, these trenches are at least 1.5 um and not more than 3 um wide.

Figure 2G:
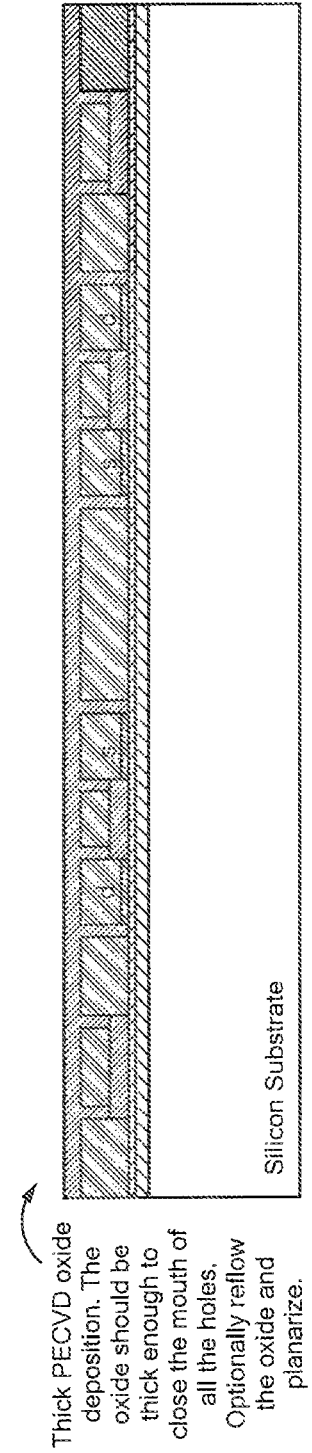

In FIG. 2G, a thick PECVD (plasma-enhanced chemical vapor deposition) oxide layer is formed so as to close all of the trenches. Preferably, this oxide layer is reflowed, e.g., to better ensure that the trenches are completely filled and to smooth out the oxide layer, and then planarized. This oxide layer will be removed later to form the gaps between the tops of the drive, sense, and shield structures and the resonant mass as well as parts of the notches 112 and parts of the spaces between the anchors and springs.

Figure 2H:
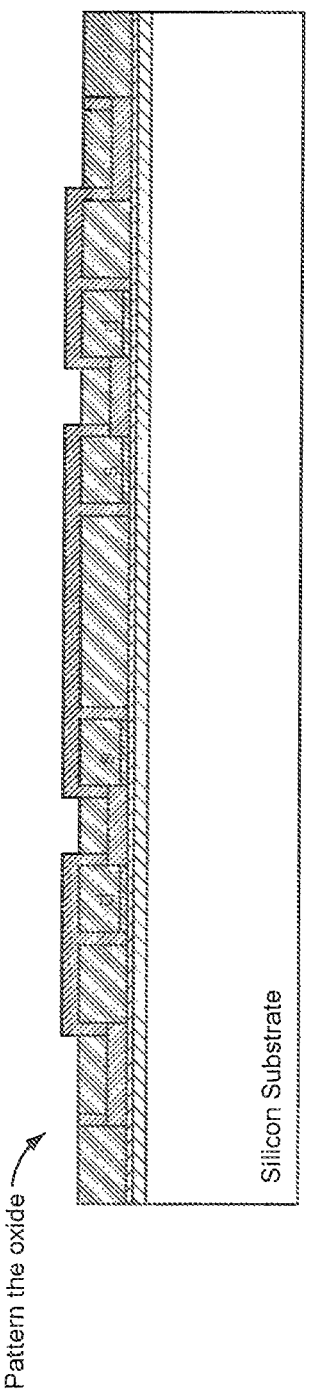

In FIG. 2H, the oxide layer is patterned so as to leave sacrificial oxide on top of the drive, sense, and shield structures.

Figure 2I:
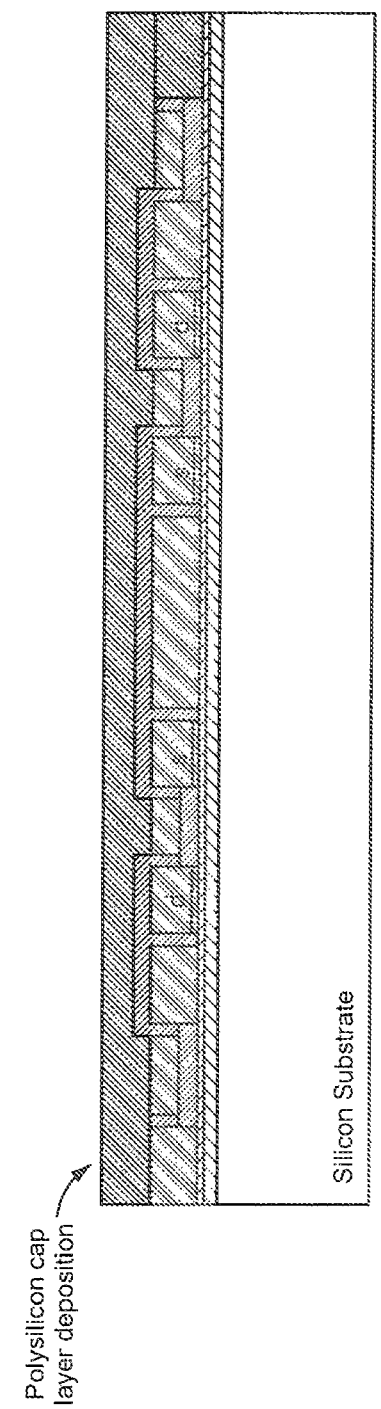

In FIG. 2I, a polysilicon layer is formed. This is essentially the cap layer that will include the resonant mass 106 and portions of the springs and anchors.

Figure 2J:
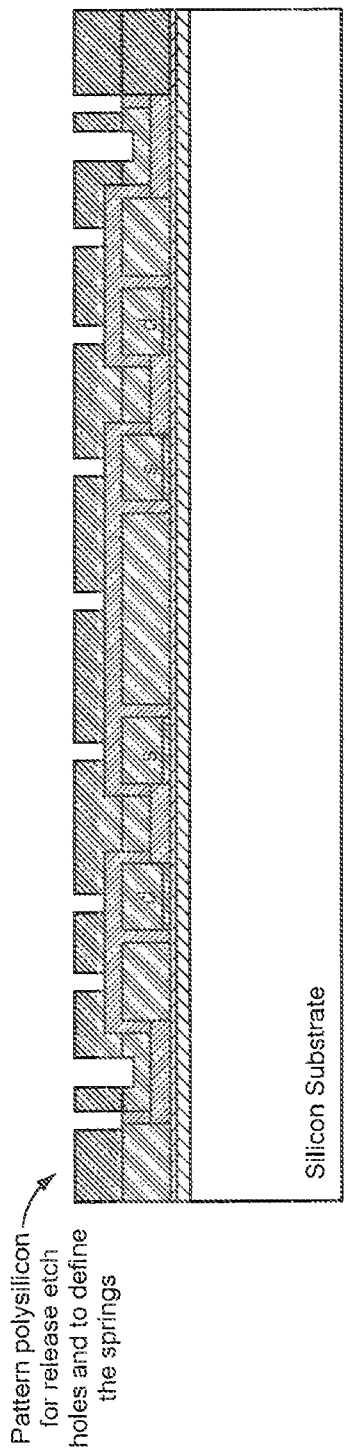

In FIG. 2J, the polysilicon layer is patterned to include release etch holes and also to define parts of the springs. It should be noted that release etch holes are formed through the resonant mass to facilitate removal of underlying sacrificial oxide.

Figure 2K:
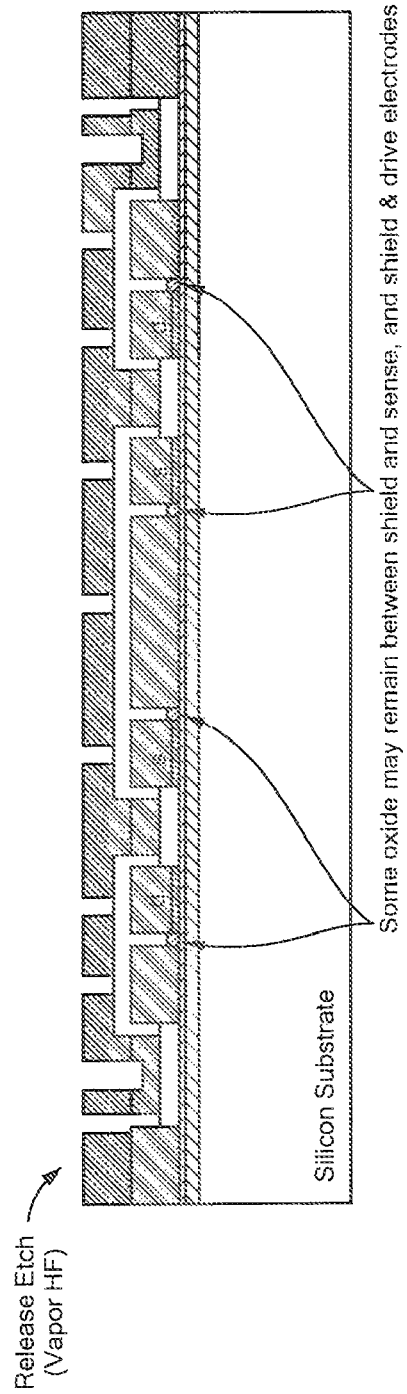

In FIG. 2K, the sacrificial oxide is removed through the release etch holes, for example, using a vapor HF (dry) etching process. It should be noted that some oxide may remain between the shield and sense structures and/or between the shield and drive structures.

Figure 2L:
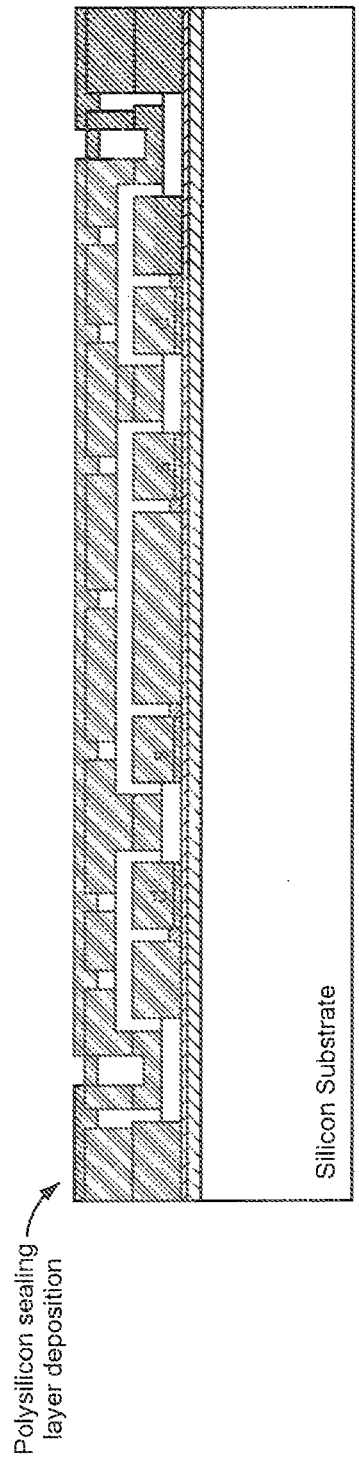

In FIG. 2L, a polysilicon sealing layer is deposited. Among other things, this sealing layer covers the release etch holes that had been formed in the resonant mass and elsewhere so as to seal the isolated cavity 116. This sealing layer also partially or completely fills the notches 112 for the springs 108. At this point, metal bond pads and associated etches may be formed.

Figure 2M:
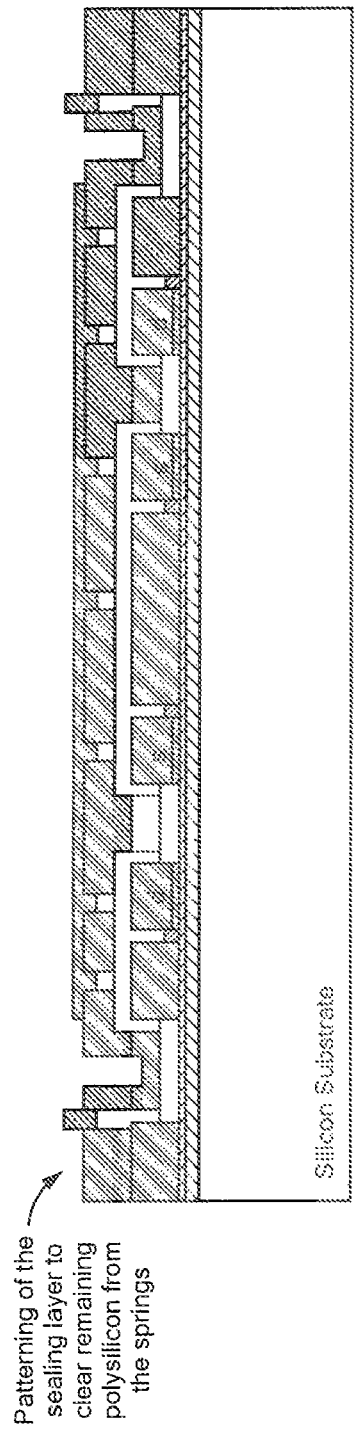

In FIG. 2M, the polysilicon sealing layer is patterned to clear the polysilicon from the notches 112, leaving polysilicon in the release etch holes and hence leaving the sealed isolated cavity 116.

It should be noted that the process described above is conceptual and that the present invention is not limited to any particular fabrication process. In practice, some of the process steps described above may be modified or omitted, and additional process steps may be included. For example, patterning of a particular material may involve deposition and subsequent removal of additional materials, such as, for example, etch stop materials, photoresist materials, and/or passivation materials, to name but a few. Also, the described process may be adapted to use other materials and may be adapted to start with a silicon-on-insulator wafer that includes an oxide layer disposed between two silicon layers. As known to those skilled in the art, anchoring on an SOI wafer may be done to a structure in the same plane as the mass or in a direction normal to this plane. Also, as discussed in more detail below, the resonator cap may be formed from a separate wafer and bonded to the substrate wafer using any of a variety of wafer-to-wafer bonding techniques.

Figure 3:
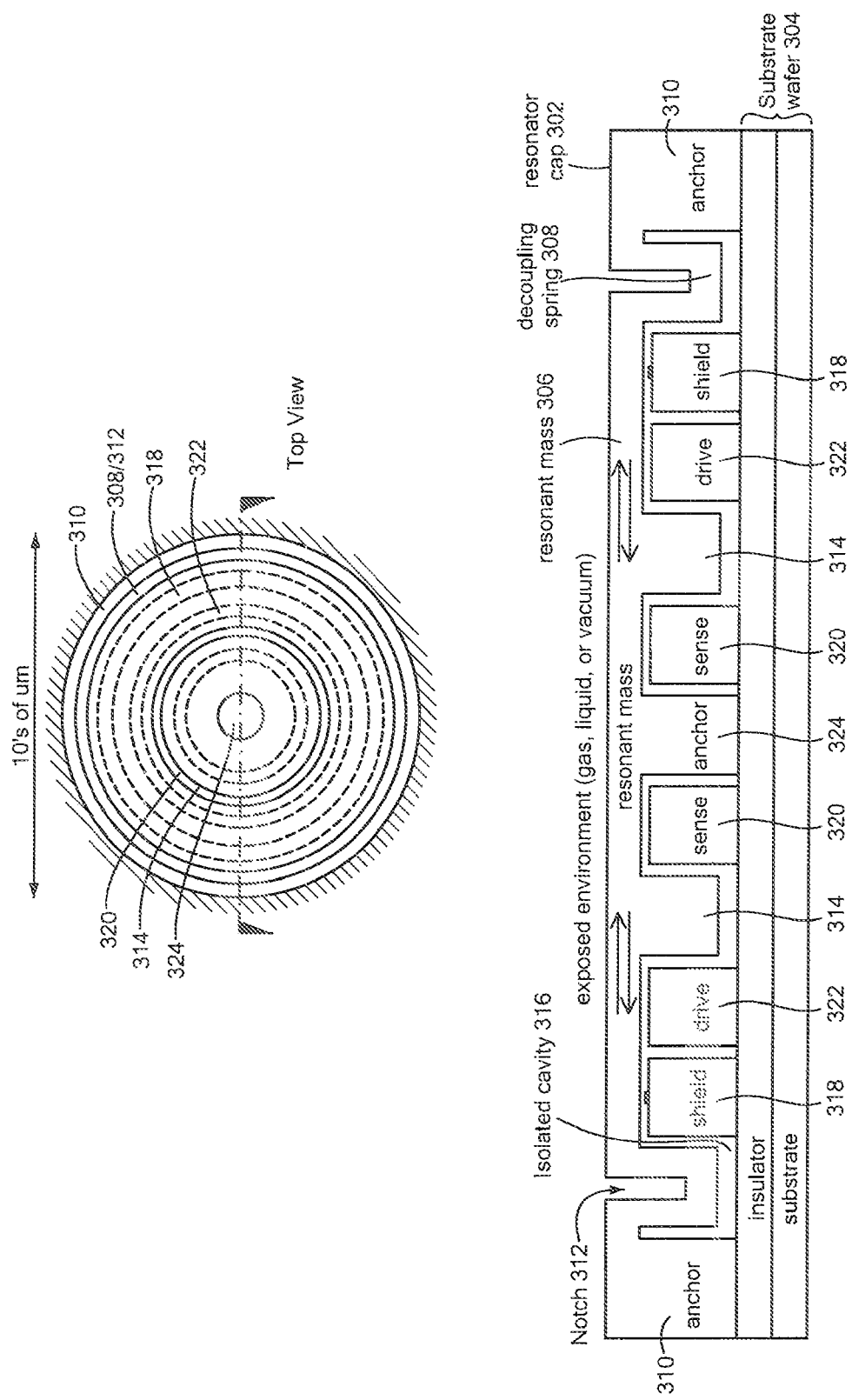
FIG. 3 is a schematic diagram showing top and cross-sectional views of a MEMS in-plane resonator that operates in a bulk acoustic contour mode, in accordance with an exemplary embodiment of the present invention.

FIG. 3 is a schematic diagram showing top and cross-sectional views of a MEMS in-plane resonator 300 that operates in a radial contour (bulk acoustic) mode, in accordance with an exemplary embodiment of the present invention. The MEMS in-plane resonator 300 includes a resonator cap 302 attached to an underlying substrate wafer 304 that includes a circular sense electrode 320, a circular drive electrode 322, and a circular shield structure 318 formed above an insulator layer. The resonator cap 302 includes a circular resonant mass 306 that is movably coupled to an anchor 310 by a circular spring 308 having a top-side notch 312 and that also is attached to the substrate wafer 314 by anchor 324. The underside of the resonant mass 306 includes a circular protrusion 314 that is capacitively coupled with the circular drive electrode 322 and circular sense electrode 320 to respectively drive and sense bulk acoustic mode resonance of the resonant mass 306. The shield structure 318 provides electrical shielding between the drive electrode 322 and the notched spring 308. In the top view, the circular structures shown in dashed lines represent (from the center outward) the sense 320, drive 322, and shield 318 structures while the circular structures shown in solid lines represent (from the center outward) the anchor 324, the circular protrusion 314, and the notched spring 308. As shown in the top view, the resonant mass 306 is surrounded by notched spring 308 and surrounding anchor 310 so as to form an isolated cavity 316 that houses the drive 322, sense 320, and shield 318 structures. It should be noted that, overall, the resonator cap 302 may be round, square, or other shape. For convenience, various structures are omitted from FIG. 3 such as, for example, electrical connections to the drive electrodes 322, sense electrodes 320, shield structures 318, and resonator cap 302.

Conceptually, the MEMS in-plane resonator 300 may be fabricated using a modified version of the fabrication process described above with reference to FIG. 2, specifically adapted to form anchor 324.

Figure 10:
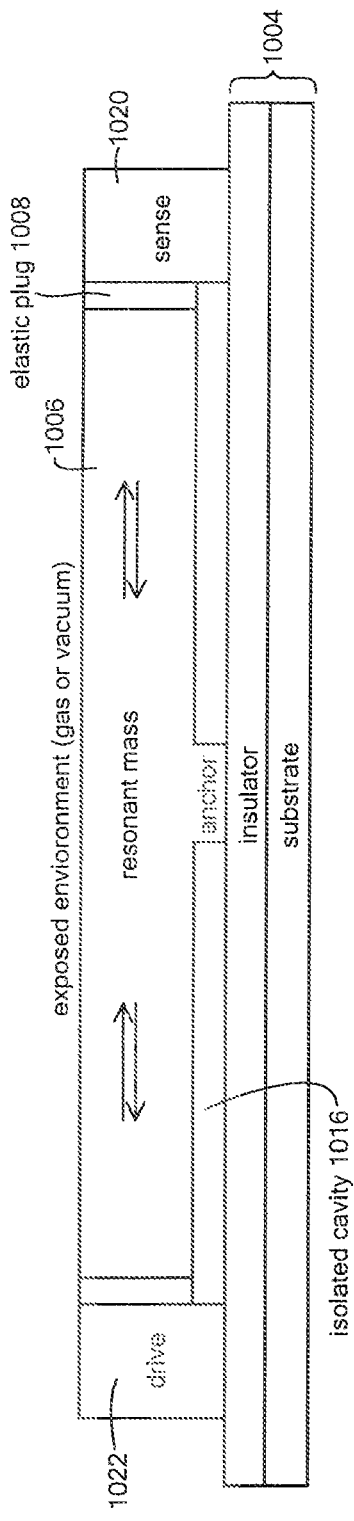
FIG. 10 is a schematic diagram showing a cross-sectional view of a lateral resonator with exposed electrodes as known in the art.

FIG. 10 is a schematic diagram showing a cross-sectional view of a lateral resonator with exposed electrodes, similar to a configuration described in U.S. Pat. No. 7,551,043 (Nguyen et al., which was incorporated by reference above), in which the elastic plug 1008 is used to decrease the motional resistance of the resonator and also to prevent particulate matter from getting caught between the resonant mass 1006 and the electrodes 1020 and 1022. In the configuration shown, this resonator operates similarly to the resonator shown in FIG. 3 but the single drive electrode 1022 and the single sense electrode 1020 are positioned adjacent to the resonant mass 1006 rather than under the resonant mass 1006 and are exposed to the external environment rather than being wholly contained with the isolated cavity 1016 between the resonant mass 1006 and the underlying substrate 1004. Such a configuration, with exposed electrodes, may work in certain environments such as a vacuum and perhaps air or other gases but may not be practical for use in liquids or in other situations where the environment and the exposed electrodes interact negatively, e.g., where a short circuit is created between the electrodes and the resonant mass so as to prevent resonance, where the environment damages or otherwise contaminates the electrodes, where the electrodes damage or otherwise contaminate the environment, or where there is an undesirable transfer of electrical charge from the electrode to the environment.

Figure 11:
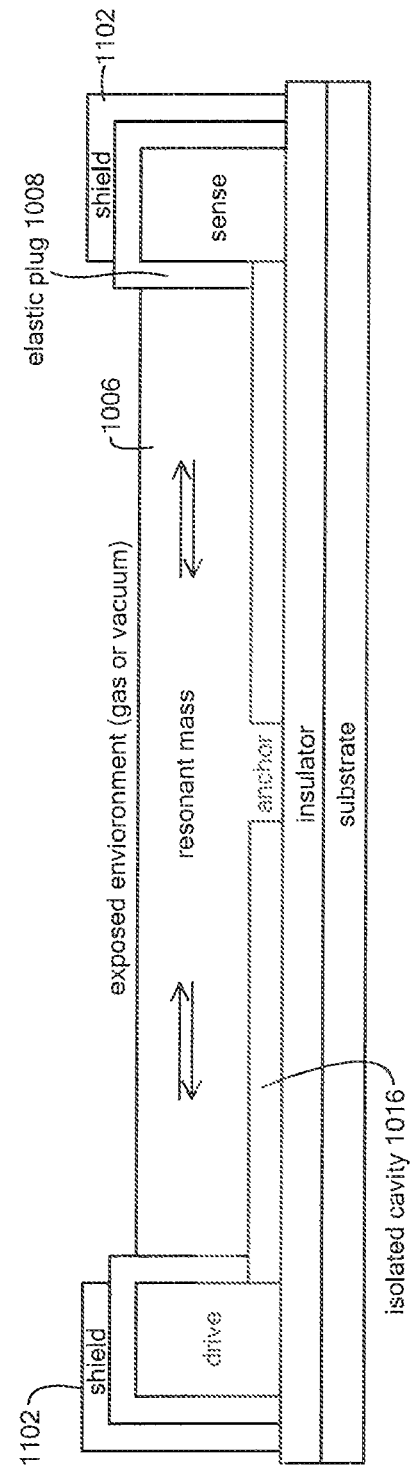
FIG. 11 is a schematic diagram showing a cross-sectional view of the lateral resonator of FIG. 10 with shielded electrodes, in accordance with an exemplary embodiment of the present invention.

Therefore, in various embodiments of the present invention, the electrodes 1020 and 1022 may be encapsulated so as to isolate them from the external environment. FIG. 11 is a schematic diagram showing a cross-sectional view of the lateral resonator of FIG. 10 with shielded electrodes, in accordance with an exemplary embodiment of the present invention. Here, the elastic material 1008 is formed over the exposed portions of the electrodes 1020 and 1022, and a shield 1102 (e.g., of a silicon-based material) is formed over a portion of the elastic material 1008 so as to support and protect the underlying elastic material 1008 while still allowing for movement of the resonant mass 1006.

Figure 4:
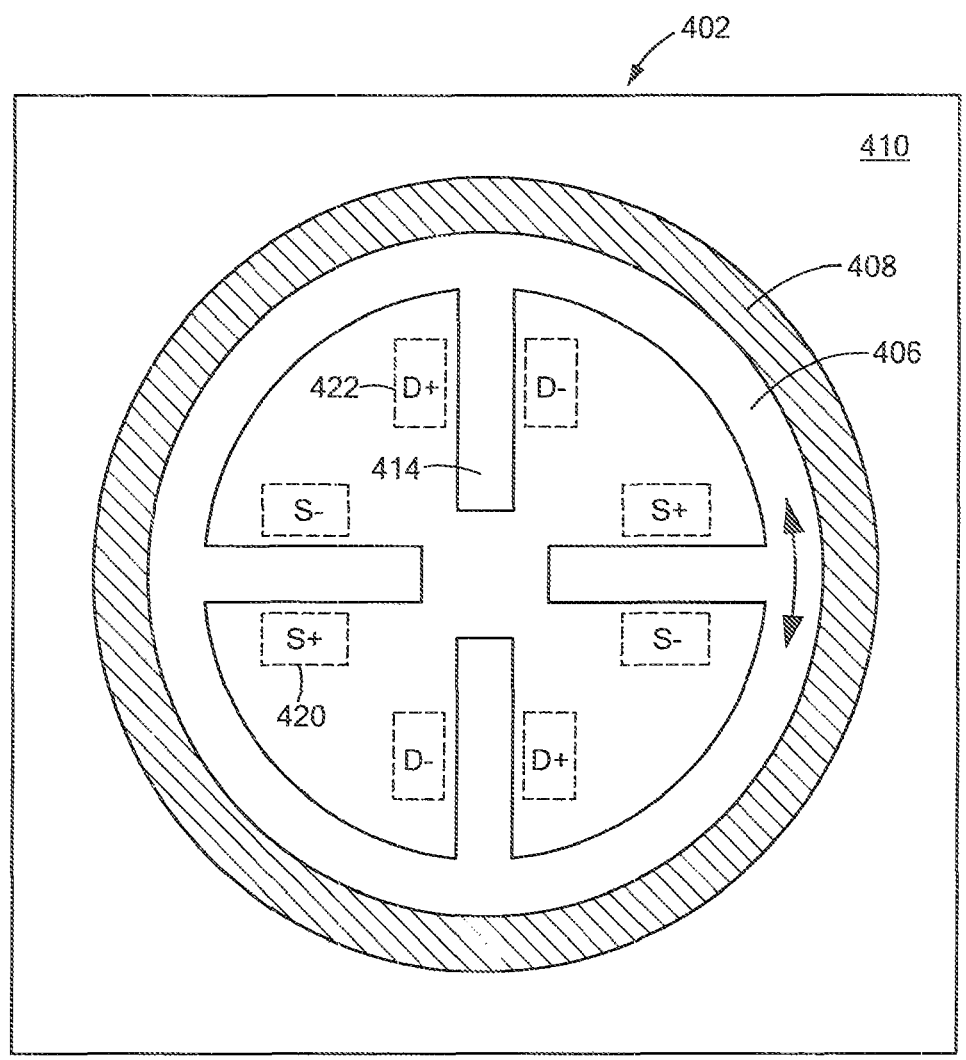
FIG. 4 is a schematic diagram showing a top view of a MEMS in-plane resonator configured to operate in a rotational mode, in accordance with an exemplary embodiment of the present invention.

FIG. 4 is a schematic diagram showing a top view of a MEMS in-plane resonator 400 configured to operate in a rotational mode, in accordance with an exemplary embodiment of the present invention. Here, the resonator cap 402 includes a circular resonant mass 406 that is movably coupled to an anchor 410 by a circular notched spring 408 (for convenience, the notch is not numbered). The resonator cap 402 is attached to the underlying substrate wafer by anchor 410. The underside of the resonant mass 406 includes radial protrusions 414 (for convenience, only one protrusion is numbered) that is capacitively coupled with the corresponding drive electrodes 422 and sense electrodes 420 to respectively drive and sense rotational resonance of the resonant mass 406. Here, the drive electrodes 422 labeled D+ operate in-phase with one another to rotate the resonant mass 406 in a counterclockwise direction while the drive electrodes 422 labeled D− operate in phase with one another and in anti-phase with the drive electrodes 422 labeled D+ to rotate the resonant mass 406 in a clockwise direction. The anchor 410 forms an isolated cavity that houses the drive 422 and sense 420 structures. It should be noted that certain embodiments may include shield structures as discussed above with reference to FIGS. 1 and 3. It should be noted that the circular resonant mass 406 may be a solid disk, as shown, or may be annular. It also should be noted that resonant masses of other shapes (e.g., square) may be configured to resonate rotationally, so a rotationally-dithered mass does not necessarily have to be round.

The embodiments described above are exemplary and are not intended to limit the present invention to a particular configuration or in-plane resonance mode. It should be noted that additional/different configurations of protrusions, drive electrodes, sense electrodes, and other structures may be used in various alternative embodiments.

In the exemplary embodiments described above, the resonant mass is movably coupled by one or more simple notched springs (e.g., essentially four springs along the sides of the resonant mass in FIG. 1, essentially one spring along the outer periphery of the resonant masses in FIGS. 3 and 4) that provide in-plane compliance and/or relieve stresses. Such notched springs are relatively easy to fabricate but may also be relatively stiff along the length of the spring, and such notched springs may permit out-of-plane movements of the resonant mass and may, in some cases, cause some amount of out-of-plane movement of the resonant mass (e.g., the edges of resonant mass 106 may move up and down as it resonates laterally). It should be noted that different spring configurations may be used in alternative embodiments, for example, to reduce spring stiffness along the length of the spring or to reduce out-of-plane movements of the resonant mass.

Figure 5:
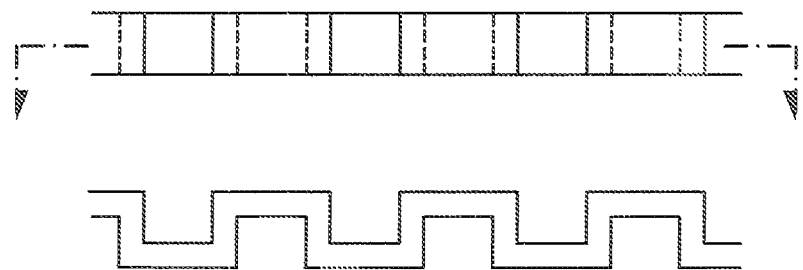
FIG. 5 is a schematic diagram showing top and cross-sectional views of an in-line spring configuration in accordance with one alternative embodiment of the present invention.

FIG. 5 is a schematic diagram showing top and cross-sectional views of an in-line spring configuration in accordance with one alternative embodiment of the present invention. Here, the spring essentially includes alternating top and bottom notches. The dashed lines represent the boundaries of notches formed in the underside of the material.

Figure 6:
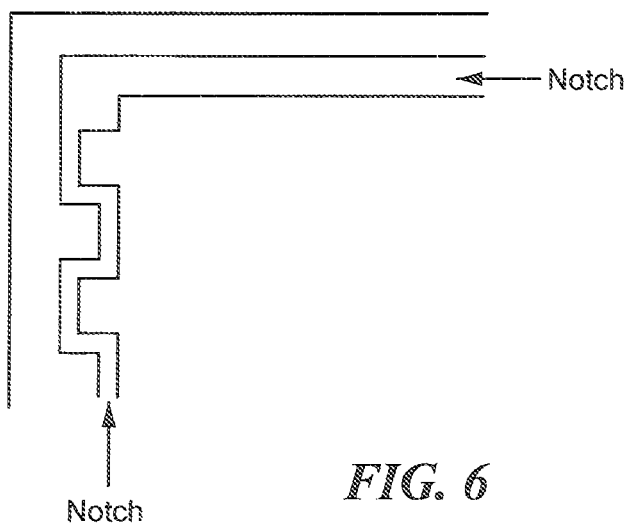
FIG. 6 is a schematic diagram showing a top view of a serpentine spring configuration in accordance with another alternative embodiment of the present invention.

FIG. 6 is a schematic diagram showing a top view of a serpentine spring configuration in accordance with another alternative embodiment of the present invention.

Such alternative spring configurations may be used, for example, along the lateral sides of the resonant mass in FIG. 1 (i.e., the sides parallel to the resonant motion) or along the periphery of the circular masses in FIGS. 3 and 4.

It should be noted that the top-side notch(es) may be filled with an elastic material to allow flexing while also sealing the spring(s) from the exposed environment. Among other things, such sealing can be done to produce a substantially flat top surface and/or to prevent contaminants (e.g., particulate matter) from entering the notch(es) and potentially interfering with operation of the resonant mass.

Figure 7:
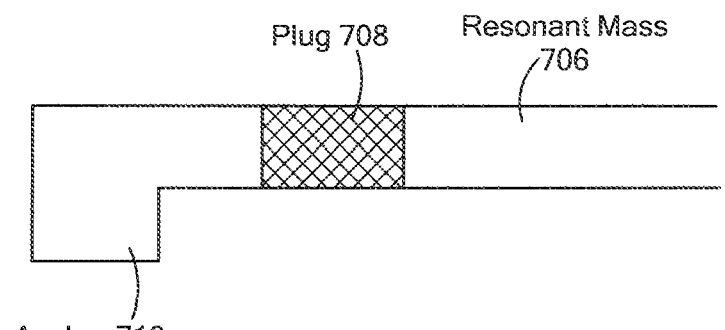
FIG. 7 is a schematic diagram showing a resonant mass movably coupled by a plug of elastic material, in accordance with an exemplary embodiment of the present invention.

Rather than using springs to movably couple the resonant mass and/or seal the device, certain alternative embodiments instead use a plug of elastic material, e.g., having a lower Young's modulus than the resonator material. FIG. 7 is a schematic diagram showing a resonant mass movably coupled by a plug of elastic material, in accordance with an exemplary embodiment of the present invention. The plug may be formed prior to release of the resonant mass, for example, by etching a notch defining the outer periphery of the resonant mass while the resonant mass is supported by an underlying sacrificial layer, depositing/patterning the elastic material within the notch, and subsequently releasing the resonant mass. The plug may be formed of an electrically insulating material so as to electrically isolate the resonant mass from the surrounding anchor. In such an embodiment, different electrical potentials may be applied to the resonant mass and the surrounding anchor.

In the exemplary embodiments described above, particularly with reference the fabrication process of FIG. 2, the resonator cap is formed in situ as part of the wafer fabrication process. In certain alternative embodiments, the resonator cap may be formed from a separate wafer and bonded to the substrate wafer using any of a variety of wafer-to-wafer bonding techniques (e.g., glass seal, metal-to-metal, etc.).

Figure 8:
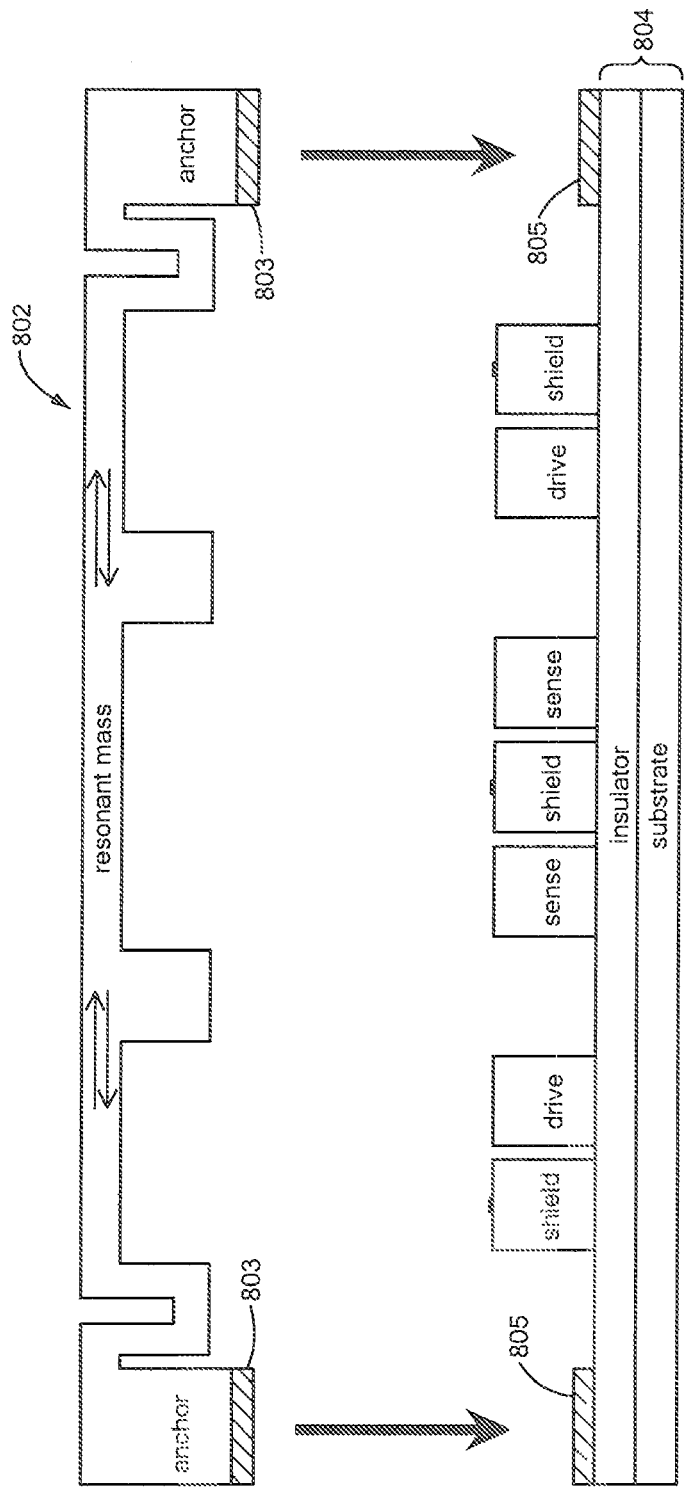
FIG. 8 is a schematic diagram showing a wafer capping embodiment, in accordance with an exemplary embodiment of the present invention.

FIG. 8 is a schematic diagram showing a wafer capping embodiment, in accordance with an exemplary embodiment of the present invention. Here, the resonator cap 802 (which, for exemplary purposes, is substantially in the form of the resonator cap 102 shown in FIG. 1) is formed from a first wafer separate from the substrate wafer 804 (which, for exemplary purposes, is substantially in the form of the substrate wafer 104 shown in FIG. 1). The two wafers are bonded to one another to produce the MEMS in-plane resonator with isolated cavity encapsulating the various drive, sense, shield, and protrusion structures. In certain embodiments, the resonator cap 102 and/or the substrate wafer 104 may include appropriate bonding materials (e.g., glass frit, solder, metallization, etc.) to facilitate or enable the wafer-to-wafer bonding. In the exemplary embodiment shown in FIG. 8, the resonator cap 802 includes a bonding material 803 on the bottom of the anchor and the substrate wafer 804 includes a bonding material 805 at the locations where bonding will occur. It should be noted that the bonding materials 803 and 805 may be the same material or may be different materials. It should be noted that the bond formed between the resonator cap 802 and the substrate wafer 804 is typically hermetic, although in alternative embodiments, a non-hermetic bond may be sealed, for example, by applying a hermetic material over the bond site.

Figure 9A:
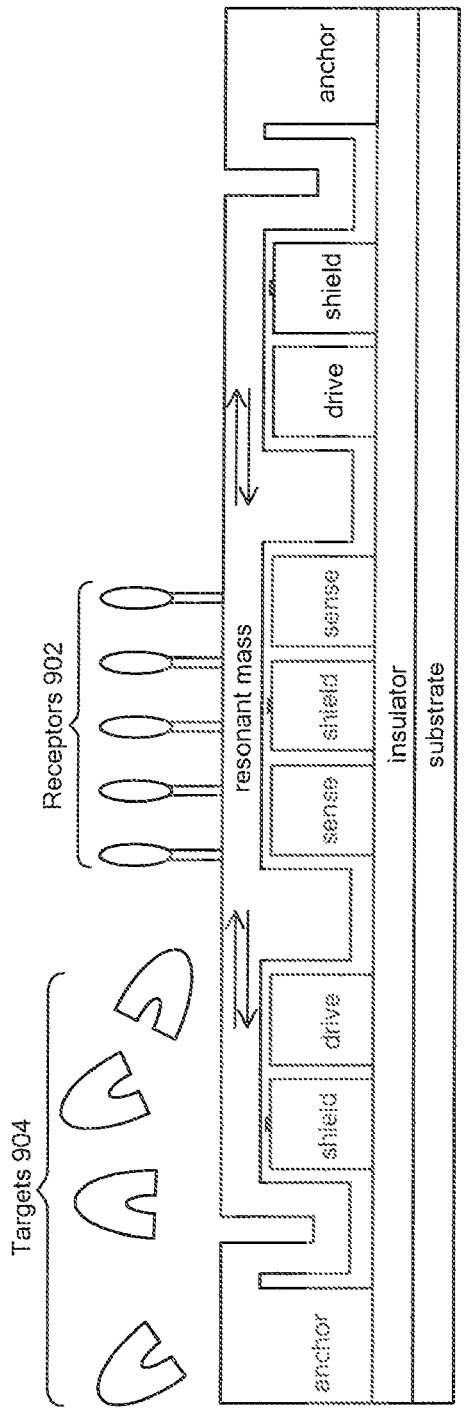
FIG. 9 is a schematic diagram showing the surface of the resonant mass coated with a receptor material for a specific chemical target that, when present in sufficient quantities in the external environment, bind to the receptor material so as to increase the moving mass of the resonator and consequently decrease the resonance frequency of the resonator, in accordance with an exemplary embodiment of the present invention.
Figure 9B:
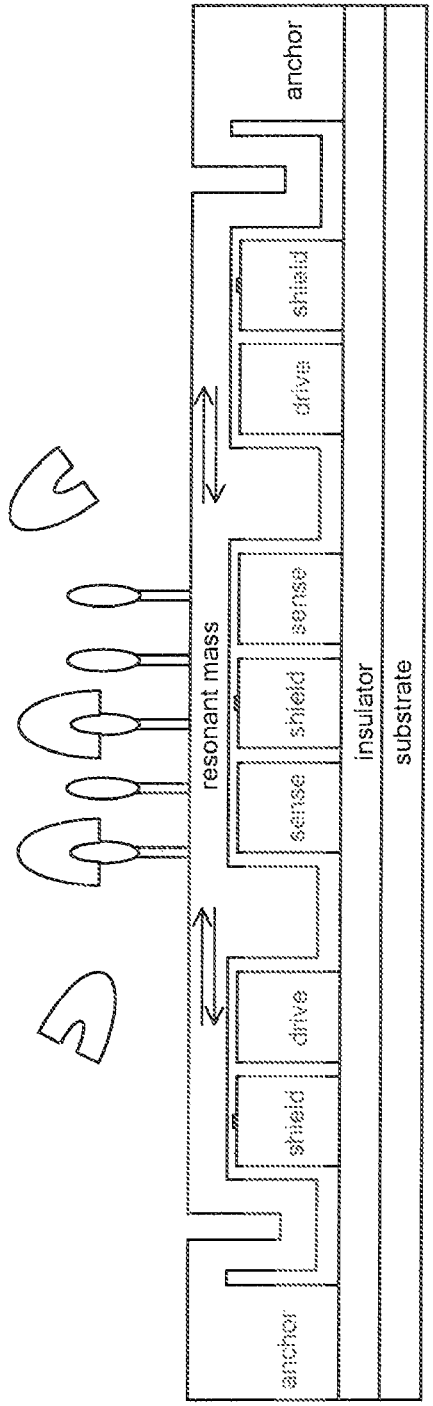

Embodiments of the present invention may be used for a variety of applications, including, among others, liquid applications (e.g., viscometry, densitometry, biological/chemical sensing) and gas sensing applications (e.g., radon, carbon monoxide, smoke, etc.). For example, as shown in FIG. 9, the surface of the resonant mass may be partially or completely coated with a receptor material 902 for a specific target (e.g., ligand) 904 that, when present in sufficient quantities in the external environment, bind to the receptor material 902 so as to increase the moving mass of the resonator and consequently decrease the resonance frequency of the resonator. Similarly, the surface of the resonant mass may be partially or completely coated with a material that dissolves or dissipates in the presence of a target (e.g., moisture, acid, etc.) so as to decrease the moving mass of the resonator and consequently increase the resonance frequency of the resonator. Such changes in resonance frequency from an increase or decrease in resonating mass can be detected and used to determine the presence and/or amount of a particular target.

Thus, the MEMS in-plane resonator typically includes, or is used in conjunction with, a drive circuit that provides drive signals to the drive electrodes based (either directly or via a phase-locked loop) on velocity feedback signals received from the sense electrodes so as to drive the resonant mass at its resonance frequency. In exemplary embodiments of the present invention, the drive circuit is configured to detect changes in resonance frequency (e.g., by measuring resonance frequency over time and comparing the resonance frequency with a baseline resonance frequency, e.g., established during device calibration, self-test, or otherwise). Characteristics of the external environment may be inferred, for example, based on the amount of change of the resonance frequency and/or the rate of change of the resonance frequency. In certain embodiments, the drive circuit may include a temperature sensor and may use temperature measurements to compensate for changes in resonance frequency due to temperature.

Additionally or alternatively, the surface of the resonant mass and/or other exposed surfaces may be partially or completely coated with materials to increase or reduce certain interactions with the external environment, such as, for example, a passivation material (e.g., to prevent damage from exposure to certain chemicals, radiation, etc.), an anti-stiction material, a hydrophilic material, a hydrophobic material, an electrical conductor or insulator material, a chemically or electrochemically active material, an adhesive material (e.g., to capture particulate matter), a polymer film that further degrades the damping performance (e.g., for gas sensing applications) or other material. In certain embodiments, interactions with the ambient may produce an electrical potential that can be sensed using appropriate sense electronics (e.g., an analog-to-digital converter).

In embodiments that include a material on the outer surface of the resonant mass or resonator cap, an intermediate material layer may be included between the surface material and the underlying resonant mass or resonator cap. For example, the intermediate layer may including an electrical insulator material, a passivation material, or other material.

In certain embodiments, raised and/or recessed features may be patterned or otherwise formed on or from the outer surface of the resonant mass, for example, to increase the surface area exposed to the external environment (e.g., to improve chemical/biological interactivity), to increase or reduce friction with the external environment (e.g., to agitate a fluid), and/or to stiffen the resonant mass. For example, the resonant mass may include corrugations, bumps, dimples, or other features.

In certain embodiments, a predetermined electrical potential may be applied to conductive surfaces that contact the ambient such as to an outer surface of the resonant mass or entire resonator cap (either directly or to a conductive material disposed on the outer surface of those structures). For example, a zero potential may be applied to reduce or eliminate electrochemical interactions or a non-zero potential may be applied to encourage electrochemical interactions. The electrical potential may be varied over time, for example, starting at one potential (e.g., zero potential) to run a calibration or self-test or make an initial measurement, and then changing to another potential (e.g., a non-zero potential) to make the surface electrochemically or electrostatically reactive. In certain embodiments, the resonant mass may be electrically isolated from the surrounding anchor structure (e.g., an elastic plug between the resonant mass and the anchor structure may be formed of an electrical insulator material) and different electrical potentials may be applied to the outer surfaces of the resonant mass and anchor structure.

In addition, alternative embodiments of the present invention may include microfluidic networks (e.g., including channels, pumps, valves, etc.) and/or sensors (electronic, mechanical, chemical, biological, drug, etc.) to support lab-on-a-chip and other applications.

As discussed above, the springs used to support and/or isolate the resonant mass may be configured to reduce or suppress out-of-plane movements of the resonant mass. Additionally or alternatively, out-of-plane movements of the resonant mass may be managed in other ways. For example, electrodes on the substrate wafer underlying portions of the resonant mass may be used to sense and/or correct out-of-plane movements electrostatically or otherwise.

Out-of-plane movements caused by imperfections in the design and/or fabrication of the various resonator components (e.g., the resonant mass, the springs, etc.), which may be proportional to the displacement and/or velocity of the resonating mass, may be reduced or suppressed in a manner similar to quadrature suppression schemes used in various MEMS gyroscopes. Some examples of quadrature suppression schemes are described by Clark in U.S. Pat. No. 5,992,233 and by Geen in U.S. Pat. No. 7,032,451, each of which is hereby incorporated herein by reference in its entirety. Quadrature suppression is also discussed in Lemkin, U.S. Pat. No. 7,051,590; in Chaumet, U.S. Patent Application Publication No. 2008/0282833; and in Saukoski, M., *System and Circuit Design for a Capacitive MEMS Gyroscope*, Doctoral Dissertation, TKK Dissertations 116, Helsinki University of Technology, Espoo, Finland (2008), each of which is hereby incorporated herein by reference in its entirety.

Out-of-plane movements caused by pressure changes in the external environment may be sensed, for example, through variable capacitance between the resonant mass and one or more electrodes on the underlying substrate, and may be used, for example, to compensate for changes in resonance frequency caused by out-of-plane movements of the resonant mass (e.g., due to stiffening of the springs or elastic plugs) or to combine resonance-frequency-based sensing (e.g., for viscosity, chemical, or biological sensing) and out-of-plane sensing (e.g., for pressure sensing) into a single MEMS device. Some examples of sensing out-of-plane movements of a mass (specifically in the context of sensing out-of-plane movements of a diaphragm of a MEMS microphone) are included in commonly-owned United States patent application publication number US2006/0237806, which is hereby incorporated by reference in its entirety.

It should be noted that embodiments of the present invention may be operated in a one-port or two-port mode. In a two-port mode, as shown, for example, in FIGS. 1, 3, 10, and 11, the resonant mass is between separate drive and sense electrodes, which tends to reduce unwanted electrical feedthrough that would not be indicative of mechanical motion. In a one-port mode, the resonant mass is used as a drive or sense electrode. Thus, for example, in a one-port configuration based on FIG. 11, sensing might be performed from the electrical node connected directly to the resonant mass.

Similarly, the drive electrodes and/or sense electrodes may be operated in a differential or single-ended manner. In FIG. 1, for example, the drive and sense electrodes are configured in a differential manner, with a pair of drive electrodes used to drive movement of the resonant mass (e.g., by placing alternating signals on the drive electrodes) and a pair of sense electrodes used to sense movement of the resonant mass (e.g., by differential signals provided by the sense electrodes). On the other hand, in FIG. 11, for example, the drive and sense electrodes are configured in a single-ended manner, with a single drive electrode used to drive movement of the resonant mass and a single sense electrode used to sense movement of the resonant mass.

Other configurations/modes are possible. Thus, the present invention is not limited to specific configurations/modes for driving and sensing the in-plane movements of the resonant mass.

While exemplary embodiments are described above with reference to electrostatic drivers and sensors, it should be noted that the present invention is not limited to electrostatic drivers and sensors, and other types of drivers and/or sensors (e.g., piezoelectric) may be used in certain embodiments. Some examples of piezoelectric drivers and sensors for use in MEMS sensors are provided in commonly-owned U.S. patent application Ser. No. 12/208,803, which is hereby incorporated herein by reference in its entirety.

It should be noted that a MEMS device may include two or more in-plane resonators of the type described above, for example, to provide redundancy or to sense different characteristics of the external environment. The resonators may be configured differently, e.g., one to measure viscosity and the other including a receptor material coating to sense for a particular target substance. Measurements from the resonators may be used independently or may be combined. The resonators may be mechanically coupled, electrically coupled, or both. For example, the output of a chemical or biological sensor may be based in part on a viscosity measurement from a viscosity sensor. Multiple resonant masses may be mechanically coupled so as to operate at a single resonance frequency and two mechanically-coupled resonant masses may be configured to resonate in-phase or in antiphase along a common axis, along or about parallel axes, or otherwise.

Thus, embodiments may include arrays of sensors of the types described herein. Sensors may be of the same or different mechanical design, functional coating, electrical connection, etc. They also may be mechanically connected, as appropriate. As discussed above, embodiments of the present invention may be fabricated using conventional surface micromachining techniques and high-volume wafer fabrication processes, widespread for fabricating MEMS sensors, to construct in-plane resonators exposed to an external environment with hermetically isolated transducers. Such a high-volume process also enable arrays of sensors to be fabricated on the same centimeter- or millimeter-scale chip with optionally integrated electronics, resulting in better selectivity and robustness as well as enhanced algorithms for signal conditioning. Thus, embodiments of the present invention may include MEMS in-plane resonators smaller than a few centimeters across and less than a few millimeters thick, allowing such device to be fabricated in large volumes and enabling their use in applications where small size is necessary or desirable.

The present invention may be embodied in other specific forms without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A MEMS sensor comprising:
a substrate wafer;
at least one resonant mass supported by the substrate wafer and configured to resonate substantially in-plane;
at least one transducer coupled to the at least one resonant mass for at least one of driving and sensing in-plane movement of the at least one resonant mass, wherein at least part of one surface of the resonant mass is configured for exposure to an environment external to the MEMS sensor and wherein the at least one transducer is isolated from the external environment, wherein the at least one transducer is at least partially contained within an isolated cavity formed at least in part by the at least one resonant mass and the substrate wafer, wherein the at least one resonant mass is part of a resonator cap attached to the substrate wafer, and wherein the resonator cap and the substrate wafer form an isolated cavity within which the at least one transducer is at least partially contained; and
a hermetic seal at an interface between the resonator cap and the substrate wafer.

2. A MEMS sensor according to claim 1, further comprising at least one transducer coupled to the at least one resonant mass for at least one of driving and sensing out-of-plane movements of the at least one resonant mass.

3. A MEMS sensor according to claim 1, further comprising at least one of a microfluidic network or sensors.

4. Apparatus comprising an array of a plurality of MEMS sensors according to claim 1.

5. Apparatus according to claim 4, wherein at least one of:
at least two sensors are of the same mechanical design;
at least two sensors are of different mechanical designs;
at least two sensors have the same functional coating;
at least two sensors have different functional coatings;
at least two sensors are mechanically coupled; or
at least two sensors are electrically coupled.

6. A MEMS sensor according to claim 1, wherein at least part of a top side of the resonant mass is configured for exposure to the external environment and wherein a bottom side of the resonant mass includes at least one protrusion configured to interoperate with the at least one transducer for at least one of driving and sensing in-plane movement of the resonant mass.

7. A MEMS sensor according to claim 1, further comprising:
a set of shield structures on the substrate wafer.

8. A MEMS sensor according to claim 1, further comprising circuitry configured to apply a predetermined electrical potential to at least one outer conductive surface exposed to the external environment.

9. A MEMS sensor according to claim 1, wherein the at least one resonant mass is movably coupled by a suspension.

10. A MEMS sensor according to claim 9, wherein the suspension includes at least one of:
a spring;
a spring having a top side notch filled with an elastic material; or
an elastic plug.

11. A MEMS sensor according to claim 1, wherein the cavity is partially or completely evacuated.

12. A MEMS sensor according to claim 1, wherein the at least one transducer includes one of:
a capacitively-coupled transducer; or
a piezoelectrically-coupled transducer.

13. A MEMS sensor according to claim 1, wherein the surface of at least one resonant mass configured for exposure to the external environment is at least partially covered by a material meant to interact with a specific type of target in the external environment, such interaction changing the moving mass of the resonant mass so as to change the resonance frequency of the resonant mass, the sensor further including circuitry configured to detect a change in resonance frequency resulting from such interaction.

14. A MEMS sensor according to claim 13, wherein the material includes one of:
an adhesive material to which the target adheres;
a chemically or electrochemically active material;
a hydrophilic material;
a receptor material to which a specific target binds; or
a material that dissolves or dissipates in the presence of the target so as to decrease the moving mass of the resonator and consequently increase the resonance frequency of the resonator.

15. A MEMS sensor according to claim 1, wherein the surface of at least one resonant mass configured for exposure to the external environment is at least partially covered by a material meant to reduce interactions with the external environment.

16. A MEMS sensor according to claim 1, further comprising circuitry configured to sense an electrical potential caused by interaction with the external environment.

17. A MEMS sensor according to claim 1, wherein the at least one resonant mass includes raised and/or recessed features patterned or otherwise formed on or from the top surface of the resonant mass.

18. A MEMS sensor according to claim 1, wherein the at least one resonant mass includes a plurality of resonant masses.

19. A MEMS sensor according to claim 18, wherein at least one of:
the surfaces of the resonant masses configured for exposure to the external environment are at least partially coated with the same material;
the surfaces of the resonant masses configured for exposure to the external environment are at least partially coated with different materials; or
the resonant masses are mechanically coupled.

20. A MEMS sensor comprising:
a substrate wafer;
at least one resonant mass supported by the substrate wafer and configured to resonate substantially in-plane; and
at least one transducer coupled to the at least one resonant mass for at least one of driving and sensing in-plane movement of the at least one resonant mass, wherein at least part of one surface of the resonant mass is configured for exposure to an environment external to the MEMS sensor and wherein the at least one transducer is isolated from the external environment, and wherein the resonant mass is movably coupled to the at least one transducer via an elastic material, and wherein portions of the at least one transducer that would otherwise be exposed to the external environment are covered with at least one material to isolate those portions from the external environment.

21. A MEMS sensor according to claim 20, wherein at least one of:
at least part of a top side of the resonant mass is configured for exposure to the external environment and a bottom side of the resonant mass includes at least one protrusion configured to interoperate with the at least one transducer for at least one of driving and sensing in-plane movement of the resonant mass;
the sensor further comprises a set of shield structures on the substrate wafer;
the sensor further comprises circuitry configured to apply a predetermined electrical potential to at least one outer conductive surface exposed to the external environment;
the at least one resonant mass is movably coupled by a suspension;
the suspension includes at least one of a spring, a spring having a top side notch filled with an elastic material, or an elastic plug;
the at least one transducer is at least partially contained within an isolated cavity formed at least in part by the at least one resonant mass and the substrate wafer;
the cavity is partially or completely evacuated;
the at least one transducer includes a capacitively-coupled transducer;
the at least one transducer includes a piezoelectrically-coupled transducer;
the surface of at least one resonant mass configured for exposure to the external environment is at least partially covered by a first material meant to interact with a specific type of target in the external environment, such interaction changing the moving mass of the resonant mass so as to change the resonance frequency of the resonant mass, the sensor further including circuitry configured to detect a change in resonance frequency resulting from such interaction;
the first material includes one of an adhesive material to which the target adheres, a chemically or electrochemically active material, a hydrophilic material, a receptor material to which a specific target binds, or a material that dissolves or dissipates in the presence of the target so as to decrease the moving mass of the resonator and consequently increase the resonance frequency of the resonator;
the surface of at least one resonant mass configured for exposure to the external environment is at least partially covered by a second material meant to reduce interactions with the external environment;
circuitry configured to sense an electrical potential caused by interaction with the external environment;
at least one resonant mass includes raised and/or recessed features patterned or otherwise formed on or from the top surface of the resonant mass;
the at least one resonant mass includes a plurality of resonant masses;
the at least one resonant mass includes a plurality of resonant masses having surfaces configured for exposure to the external environment that are at least partially coated with the same material;
the at least one resonant mass includes a plurality of resonant masses having surfaces configured for exposure to the external environment that are at least partially coated with different materials;
the at least one resonant mass includes a plurality of resonant masses that are mechanically coupled;
the sensor further comprises at least one transducer coupled to the at least one resonant mass for at least one of driving and sensing out-of-plane movements of the at least one resonant mass;
the sensor further comprises a microfluidic network; or
the sensor further comprises at least one active sensor.

22. A MEMS sensor comprising:
a substrate wafer;
at least one resonant mass supported by the substrate wafer and configured to resonate substantially in-plane; and at least one transducer coupled to the at least one resonant mass for at least one of driving and sensing in-plane movement of the at least one resonant mass, wherein at least part of one surface of the resonant mass is configured for exposure to an environment external to the MEMS sensor and wherein the at least one transducer is isolated from the external environment, wherein the surface of at least one resonant mass configured for exposure to the external environment is at least partially covered by a material meant to interact with a specific type of target in the external environment, such interaction changing the moving mass of the resonant mass so as to change the resonance frequency of the resonant mass, the sensor further including circuitry configured to detect a change in resonance frequency resulting from such interaction.

23. A MEMS sensor according to claim 22, wherein the material includes one of:
an adhesive material to which the target adheres;
a chemically or electrochemically active material;
a hydrophilic material;
a receptor material to which a specific target binds; or
a material that dissolves or dissipates in the presence of the target so as to decrease the moving mass of the resonator and consequently increase the resonance frequency of the resonator.

24. A MEMS sensor according to claim 22, wherein at least one of:
at least part of a top side of the resonant mass is configured for exposure to the external environment and a bottom side of the resonant mass includes at least one protrusion configured to interoperate with the at least one transducer for at least one of driving and sensing in-plane movement of the resonant mass;
the sensor further comprises a set of shield structures on the substrate wafer;
the sensor further comprises circuitry configured to apply a predetermined electrical potential to at least one outer conductive surface exposed to the external environment;
the resonant mass is movably coupled to the at least one transducer via an elastic material and portions of the at least one transducer that would otherwise be exposed to the external environment are covered with at least one material to isolate those portions from the external environment;
the at least one resonant mass is movably coupled by a suspension;
the suspension includes at least one of a spring, a spring having a top side notch filled with an elastic material, or an elastic plug;
the at least one transducer is at least partially contained within an isolated cavity formed at least in part by the at least one resonant mass and the substrate wafer;
the cavity is partially or completely evacuated;
the at least one transducer includes a capacitively-coupled transducer;
the at least one transducer includes a piezoelectrically-coupled transducer;
the surface of at least one resonant mass configured for exposure to the external environment is at least partially covered by a second material meant to reduce interactions with the external environment;
circuitry configured to sense an electrical potential caused by interaction with the external environment;
at least one resonant mass includes raised and/or recessed features patterned or otherwise formed on or from the top surface of the resonant mass;
the at least one resonant mass includes a plurality of resonant masses;
the at least one resonant mass includes a plurality of resonant masses having surfaces configured for exposure to the external environment that are at least partially coated with the same material;
the at least one resonant mass includes a plurality of resonant masses having surfaces configured for exposure to the external environment that are at least partially coated with different materials;
the at least one resonant mass includes a plurality of resonant masses that are mechanically coupled;
the sensor further comprises at least one transducer coupled to the at least one resonant mass for at least one of driving and sensing out-of-plane movements of the at least one resonant mass;
the sensor further comprises a microfluidic network; or
the sensor further comprises at least one active sensor.

* * * * *